United States Patent
Bi et al.

(10) Patent No.: US 8,350,072 B2
(45) Date of Patent: Jan. 8, 2013

(54) METHOD FOR PRODUCING SOLUBLE NEODYMIUM CHLORIDE COMPLEX

(75) Inventors: Jifu Bi, Changchun (CN); Xuequan Zhang, Changchun (CN); Liansheng Jiang, Changchun (CN); Hongguang Cai, Changchun (CN); Bei Wang, Changchun (CN); Chunyu Zhang, Changchun (CN); Lihua Na, Changchun (CN); Quanquan Dai, Changchun (CN); Changliang Fan, Changchun (CN)

(73) Assignee: CHangchun Institute of Applied Chemistry Chinese Academy of Sciences, Changchun, Jilin Province (CN)

( * ) Notice: Subject to any disclaimer, the term of this patent is extended or adjusted under 35 U.S.C. 154(b) by 282 days.

(21) Appl. No.: 12/917,892

(22) Filed: Nov. 2, 2010

(65) Prior Publication Data

US 2011/0160473 A1    Jun. 30, 2011

(30) Foreign Application Priority Data

Dec. 28, 2009    (CN) .......................... 2009 1 0218124

(51) Int. Cl.
*C07F 15/04*    (2006.01)
(52) U.S. Cl. ........................................................ 556/13
(58) Field of Classification Search ........................ None
See application file for complete search history.

(56) References Cited

FOREIGN PATENT DOCUMENTS
EP    0994131 A1    4/2000

OTHER PUBLICATIONS

Ren, Changyou, Investigation on characteristics of isoprene polymerization with neodymium chloride complex, Graduate University of Chinese Academy of Sciences, Jun. 2006.
Kwag, Gwanghoon et al., Morphology and activity of nanosized $NdCl_3$ catalyst for 1,3-butadiene polymerization, Journal of Applied Polymer Science, vol. 97, 1279-1283 (2005).
Jun, Ouyang, Rare Earth Catalyst and Polymerization, Jilin Science and Technology Press, Oct. 1991, pp. 141-143.
Chen, Wenqi, The catalytic activity of the rare earth compound with different coordination groups in polymerization of isoprene, Essays of Rubber Synthesis Catalyzed by Rare Earth, Science Press, Dec. 1980, pp. 113-123.

*Primary Examiner* — Porfirio Nazario Gonzalez
*Assistant Examiner* — James Meadows
(74) *Attorney, Agent, or Firm* — Knobbe, Martens, Olson & Bear, LLP

(57)    ABSTRACT

The invention provides a method for producing soluble neodymium chloride complex using neodymium chloride aqueous solution as raw material, thereby avoiding the use of anhydrous neodymium chloride, simplifying the synthesis process and reducing the cost for synthesizing neodymium chloride complex. The neodymium chloride complex produced by this method is soluble not only in polar solvent, but also in nonpolar solvent. Such neodymium chloride complex also has good dissolvability in aliphatic hydrocarbon solvent which has relatively weaker solution power, and even in aliphatic hydrocarbon solvent with 6 or less carbon atoms which has even lower solution power. Since neodymium chloride complex is soluble in aliphatic hydrocarbon solvent, its transportation may be conducted, which is convenient for industrial application and contributes to improve the utilization efficiency of rare earth.

5 Claims, No Drawings

METHOD FOR PRODUCING SOLUBLE NEODYMIUM CHLORIDE COMPLEX

CROSS-REFERENCE TO RELATED PATENT APPLICATION

This application claims the benefit of Chinese Patent Application Number 200910218124.6 filed on Dec. 28, 2009, the disclosure of which is hereby expressly incorporated by reference in its entirety and hereby expressly made a portion of this application.

FIELD OF THE ART

The invention relates to a method for producing soluble neodymium chloride complex.

BACKGROUND OF THE ART

Rare earth element has wide application. In the 1960's, Chinese scientists first used rare earth complex as polymerizing catalyst. Research has shown that neodymium element has the highest polymerizing activity, thus, the rare earth with high content of neodymium element is frequently used as polymerizing catalyst. Because rare earth has similar qualities and is hard to separate, in the field of polymerizing catalyst, neodymium catalyst is commonly called rare earth catalyst, while neodymium chloride complex is commonly called rare earth chloride complex. Most rare earth chloride complexes are synthesized from anhydrous rare earth chloride; only very few may be synthesized from rare earth chloride with crystal water in ethanol. Therefore, most rare earth chloride complex synthesis is inconvenient and costly.

Rare earth chloride complex is insoluble in nonpolar carbon-hydrogen solvent. Rather, they can only be used in a solid form, thus the effective utilization ratio of rare earth chloride complex is very low. Due to the insolubility of rare earth chloride-ethanol complex in aliphatic hydrocarbon solvent, its effective utilization ratio is merely 0.7% when rare earth chloride-ethanol complex is used as a catalyst component for catalyzing the polymerization of diene (Rare Earth Catalyst and Polymerization, Jun Ouyang, p. 143).

The most effective way to improve the effective utilization ratio of rare earth chloride complex is to improve the dispersibility of rare earth chloride complex so as to achieve homogeneous phase dispersion. At the same time, a key technique to lower the synthesis cost and to simply the synthesis process is to avoid using anhydrous rare earth chloride as the raw material to produce rare earth chloride complex. Researchers worldwide have conducted extensive research to solve these problems, but still failed to avoid using anhydrous rare earth chloride as the raw material, thus failed to produce rare earth chloride complex that is soluble in aliphatic hydrocarbon solvent.

Researchers outside China first dissolved anhydrous rare earth chloride in tetrahydrofuran polar solvent, then dropped such solution into hexane with high-speed stirring to produce rare earth chloride complex nanoparticles. (Kwag G., Kim D., Lee S., Bac C., Morphology and Activity of Nanosized $NdCl_3$ Catalyst for 1,3-Butadiene Polymerization, J. Appl. Polym. Sci., 2005, 97:1278-1283.). Although such complex may be made into nanoparticles, it is still insoluble, and further, a large amount of tetrahydrofuran was used during the synthesis, causing an environmental problem.

Chinese researchers used anhydrous rare earth chloride to produce higher alcohol complex. Such complex may be in a form of semitranslucent colloid in carbon-hydrogen solvent (Investigation on the reactive features of isoprene polymerization from rare earth complex, Changyou Ren, M. S. thesis of Chinese Academy of Sciences). The anhydrous rare earth chloride-higher alcohol complex dispersed in hexane and formed colloid. However, precipitation was observed after three days, which means that it was not truly dissolved in hexane.

Rare earth chloride-tributyl phosphate complex is soluble in aromatic hydrocarbon solvent (EP 0994131A$_1$), but it is produced from anhydrous rare earth chloride. Although rare earth chloride-neutral phosphate complex may be produced from rare earth chloride with crystal water (The catalytic activity of the rare earth compound with different coordination groups in polymerization of isoprene, Wenqi Chen, Essays of rubber synthesis catalyzed by rare earth. p. 113), aromatic hydrocarbon is used as a solvent in the synthesis process, and aromatic hydrocarbon is widely known for its severe toxic effect on the environment.

DISCLOSURE OF THE INVENTION

The invention provides a method for producing soluble neodymium chloride complex. In such method, neodymium chloride aqueous solution and dialkyl phosphite, as raw materials, are reacted under the technical conditions provided in the invention. The reaction product obtained from the above reaction has features similar to an amorphous form, so it cannot be crystallized to determine the detailed structure of such reaction product. Also, this invention provides a producing method that involves different concepts from routine methods, thus the resultant reaction product has unique features, incurring certain difficulties in determining the structure of the reaction product. However, the resultant neodymium chloride-dialkyl phosphite complex is analyzed by chemical analytical methods. Based on the experimental facts and data analysis, it may be determined that such reaction product is neodymium chloride-dialkyl phosphite complex. Further research is needed to determine the structure and qualitative features of such complex.

The neodymium chloride-dialkyl phosphite complex obtained from the inventive producing method is not only soluble in polar solvent, but also in nonpolar polar solvent. It also has good dissolvability in aliphatic hydrocarbon solvent which has relatively weaker solution power, and even in aliphatic hydrocarbon solvent with 6 or less carbon atoms which has even lower solution power.

The inventive method for producing soluble neodymium chloride complex comprises the following steps: mixing neodymium chloride aqueous solution, alcohol and dialkyl phosphite in a reactor to form a homogeneous phase system; letting the system to react at a temperature of 10-150° C., preferably 20-100° C., for 5 minutes to 12 hours, wherein the molar ratio of dialkyl phosphite to neodymium chloride is in a range of 0.5-60, preferably 1.0-10, and the ratio of the alcohol to the neodymium chloride aqueous solution is in a range of 3.0-30 by volume; and removing water and alcohol out of the system to obtain a neodymium chloride-dialkyl phosphite complex.

Said neodymium chloride aqueous solution is either saturated or nonsaturated neodymium chloride aqueous solution.

Said alcohol is selected from the group consisting of methanol, ethanol, propanol, or the mixtures thereof, preferably ethanol. Alcohol is a disperse medium that renders sufficient contact between dialkyl phosphite and rare earth chloride aqueous solution. It also helps in the process of removing the water so to have the water sufficiently removed. This method does not exclude the combination of alcohol and neodymium chloride aqueous solution in a ratio of more than 30 by volume, but the producing cost will increase as the usage amount of alcohol increases.

Said dialkyl phosphite has the structure shown below:

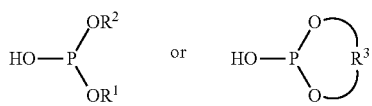

$R^1$ and $R^2$ each independently represents alkyl group with 1 or more carbon atoms, $R^3$ is an alkylidene group with 2 or more carbon atoms; preferably $R^1$ and $R^2$ each independently has 4 or more carbon atoms, $R^3$ has 7 or more carbon atoms.

Dissolubility is the ability of one substance to dissolve in another substance, which is usually decided by observing the dissolution phenomenon. Dissolubility is categorized as easily soluble, soluble, slightly soluble, and insoluble, etc. In this invention, the dissolubility of neodymium chloride-dialkyl phosphite complex is determined by observing whether the complex can disperse in the solvent to form a homogeneous phase solution. The dissolubility of the neodymium chloride-dialkyl phosphite complex produced in Examples 1-3 are shown below:

| Example | Solvent | Dissolution phenomenon | Status of solution |
|---|---|---|---|
| 1 | hexane | Dissolution | Light purple-blue homogeneous phase hexane solution |
| 2 | hexane | Dissolution | Light purple-blue homogeneous phase hexane solution |
| 3 | tetrahydrofuran | Dissolution | Light purple-blue homogeneous phase tetrahydrofuran solution |

Above data indicate that the inventive method can produce not only the neodymium chloride-dialkyl phosphite complex that is soluble in polar solvent, but also the neodymium chloride-dialkyl phosphite complex that is soluble in aliphatic hydrocarbon solvent.

In the invention, the obtained neodymium chloride-dialkyl phosphite complex is analyzed by chemical analytical methods. In Example 1, the hexane solution of neodymium chloride-diisooctyl phosphite complex contained 54.5 mmol/L of neodymium, 162.4 mmol/L of chlorine, and 166.2 mmol/L of phosphorus. Further calculation showed that the hexane solution of neodymium chloride-diisooctyl phosphite complex contained 10.9 mmol of neodymium by weight, the molar ratio of chlorine to neodymium was 2.98, of phosphorus to neodymium was 3.05. The rare earth chloride aqueous solution added before the reaction contained 10.93 mmol of neodymium, and rare earth chloride reacted completely to generate neodymium chloride-diisooctyl phosphite complex that contained chlorine and neodymium in a molar ratio of 2.98, thus indicating that none of chlorine was lost in the reaction, and the produced neodymium chloride-diisooctyl phosphite complex was neodymium trichloride-diisooctyl phosphite complex containing phosphorus and neodymium in a molar ratio of 3.05, which matched the molar ratio of diisooctyl phosphite to neodymium chloride added at the beginning of reaction, thus indicating that none of diisooctyl phosphite was lost in the reaction process.

The soluble neodymium chloride complex produced by the inventive producing method has features similar to an amorphous form. The data of Example 1 shows that the transparent purple-blue viscid reaction product obtained from the reaction which is carried out at 70° C. solidifies into transparent purple-blue solid when cooled down to 10° C.; and the formed transparent purple-blue solid further softens into transparent purple-blue viscid substance gradually as the temperature is raised to 50° C. Such features shown by the reaction product are quite similar to those of glass. Therefore, it is indicated that the neodymium chloride complex produced by the inventive method for producing soluble neodymium chloride complex is a unique complex, which relates to the unique features of the inventive producing method and dialkyl phosphite itself. The neodymium chloride complex produced in the invention cannot be crystallized to characterize its structure, since it has the features similar to an amorphous form.

The produced neodymium chloride-dialkyl phosphite complex is analyzed by chemical analytical methods. Based on the experimental facts and data analysis, it can be determined that the reaction product is neodymium chloride-dialkyl phosphite complex. The facts in Examples 1 and 2 demonstrate that the product obtained from the reaction between neodymium chloride and dialkyl phosphite is soluble in aliphatic hydrocarbon solvent. The data analysis in Example 1 shows that all the rare earth elements added before the reaction is soluble in hexane, and the molar ratio of chlorine to neodymium in such hexane was 2.98, thereby indicating that the structure of the reaction product comprises 1 molecule of neodymium and 3 molecules of chlorine. Neodymium trichloride itself is insoluble in hexane solvent, but can become soluble in hexane only when neodymium trichloride is allowed to form soluble neodymium chloride complex. In the producing process, ethanol is added as a disperse medium, which may cause the formation of neodymium chloride-alcohol complex. However, it is indicated in some literature that neodymium chloride-ethanol complex is insoluble in aliphatic hydrocarbon solvent. Therefore, the only conclusion is that coordination reaction occurs between dialkyl phosphite and neodymium chloride so as to form neodymium chloride-dialkyl phosphite complex, thereby resulting dissolution in hexane solvent.

ADVANTAGEOUS EFFECTS

The invention provides a method for producing soluble neodymium chloride complex, wherein neodymium chloride aqueous solution is used as the raw material in order to avoid the use of anhydrous neodymium chloride, simplify the synthesis process, and lower the synthesis cost of the neodymium chloride complex.

Since rare earth complex is soluble in aliphatic hydrocarbon solvent, its transportation may be conducted, which is convenient for industrial application. Although the rare earth complex produced by prior art is soluble in polar solvent or aromatic hydrocarbon solvent, both of these solvents destroy the active center when rare earth complex is used as coordination catalyst, and aromatic hydrocarbon solvent and most polar solvent are not environment friendly. On the other hand, aliphatic hydrocarbon solvent is relatively more friendly to the environment and commonly used as solvent in large-scale industrial polymerization production. In view of the above, the invention endows the dissolvability of neodymium chloride complex in aliphatic hydrocarbon solvent, which is convenient for the application of neodymium chloride complex and contributes to improve the utilization efficiency of rare earth.

For dialkyl phosphite itself, there exists a balance between the two structural forms shown below:

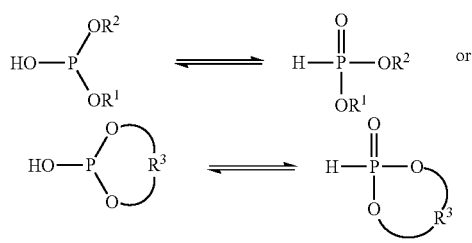

Therefore, there exist coordination reactions between rare earth chloride and these two structural forms of dialkyl phosphite: (1) when in dialkyl phosphite, $R^1$ and $R^2$ each independently represents alkyl groups with 1 or more carbon atoms and $R^3$ is an alkylidene group with 2 or more carbon atoms, as well as the molar ratio of dialkyl phosphite to neodymium chloride is more than 0.5, dialkyl phosphite may coordinate with neodymium chloride in aqueous medium, thereby generating transparent homogeneous phase of neodymium chloride-dialkyl phosphite complex, and the obtained complex is soluble in polar solvent;

(2) when in dialkyl phosphite structure, $R^1$ and $R^2$ each independently represents alkyl group having 4 or more carbon atoms and $R^3$ represents an alkylidene group with 7 or more carbon atoms, as well as the molar ratio of dialkyl phosphite to neodymium chloride is more than 1.0, neodymium chloride-dialkyl phosphite complex is generated in the reaction, and the obtained complex is soluble in aliphatic hydrocarbon solvent;

(3) In dialkyl phosphite structure, $R^1$ and $R^2$ each independently represents an alkyl group with 4 or more carbon atoms and $R^3$ represents an alkylidene group having 7 or is more carbon atoms, and particularly dialkyl phosphite is selected from the group consisting of dibutyl phosphite and isomeric alkyl esters thereof, diamyl phosphite and isomeric alkyl esters thereof, dihexyl phosphite and isomeric alkyl esters thereof, diheptyl phosphite and isomeric alkyl esters thereof, dioctyl phosphite and isomeric alkyl esters thereof, dinonyl phosphite and isomeric alkyl ester thereof, decabutyl phosphite and isomeric alkyl esters thereof, cyclopentyl phosphite and isomeric alkyl esters thereof, cycloheptyl phosphite and isomeric alkyl esters thereof, cyclooctyl phosphite and isomeric alkyl esters thereof, cyclononyl phosphite and isomeric alkyl esters thereof, cyclodecyl phosphite and isomeric alkyl esters thereof, or the mixtures thereof. When in dialkyl phosphite, $R^1$, $R^2$ or $R^3$ has more than 10 carbon atoms, neodymium chloride-dialkyl phosphite complex obtained from the reaction is soluble in aliphatic hydrocarbon solvent, but the cost is higher. Said aliphatic hydrocarbon solvent is aliphatic hydrocarbon solvent with 5 or more carbon atoms, preferably a mixed solvent containing aliphatic hydrocarbon solvent with 5-10 carbon atoms or aliphatic hydrocarbon solvent with 5-12 carbon atoms.

In the invention, the neodymium chloride complex that is soluble in aliphatic hydrocarbon solvent is also soluble in other polar solvents and aromatic hydrocarbon solvents. It is well known that rare earth chloride, as a salt, is insoluble in aliphatic hydrocarbon solvent; whereas rare earth chloride complex, as a polar metal complex, is soluble in polar solvent, and certain rare earth chloride complex is soluble in aromatic hydrocarbon solvent. However the rare earth chloride complex that is soluble in aliphatic hydrocarbon solvent has not been discovered until the current invention. Since aliphatic hydrocarbon is a poor solvent for rare earth chloride complex, dissolution of rare earth chloride complex in aliphatic hydrocarbon is a very difficult task. The invention utilizes the structural features of dialkyl phosphite itself. Therefore, the neodymium chloride complex produced by the inventive method is not only soluble in aliphatic hydrocarbon solvent, but also has excellent dissolubility in aromatic hydrocarbon solvent and polar solvent.

The neodymium chloride complex provided by the invention may be produced from a wide range of raw materials. Generally, all the methods for synthesizing rare earth chloride complex must utilize anhydrous rare earth chloride. However, anhydrous rare earth chloride is easily humidified, thus it is hard to be stored and requires a stringent condition while being handled. Rare earth chloride exists in a form of crystal water, so it is necessary to remove the crystal water completely in order to obtain anhydrous rare earth chloride. Nevertheless during the crystal water removal process, rare earth chloride is very easy to be hydrolyzed into rare earth oxychloride and hydrogen chloride is generated, which pollutes the environment. As a result, the process for producing anhydrous rare earth chloride is complicated, controlling requirement is stringent, and the cost for anhydrous rare earth chloride is very high.

DETAILED EMBODIMENTS OF THE INVENTION

EXAMPLE 1

Ten milliliter of 1.0933M neodymium chloride aqueous solution was precisely measured out by a 10 ml pipette and added into a 500 ml-round bottomed flask, into which 300 ml ethanol was added and mixed well. Then, 10.8 ml (32.8 mmol) diisooctyl phosphite was measured out by a pipette and added into the above round bottomed flask. After mixed thoroughly, the mixed solution was in purple-red. The round bottomed flask was placed and heated to react in a 70° C. water bath for 1 h before vacuumed. Then ethanol and water were removed, and the transparent purple-blue viscid reaction product was obtained. As the temperature of the water bath was cooled down to 10° C., the transparent purple-blue viscid reaction product solidified into transparent purple-blue solid. The formed transparent purple-blue solid softened into transparent purple-blue viscid substance gradually as the temperature was then raised back to 50° C. Into the round bottomed flask, 150 ml hexane was added and mixed. The transparent purple-blue viscid reaction product dispersed into hexane gradually and formed a light purple-blue homogeneous phase hexane solution. All of the light purple-blue homogeneous phase hexane solution was transferred into a 200 ml volumetric flask and further diluted with hexane to reach the volumetric mark. After the constant volume was achieved, the hexane solution of the reaction product was sealed and stored in a long neck ampoule. Based on further analysis, it was found that the hexane solution of the reaction product contained 54.5 mmol/L of neodymium, 162.4 mmol/L of chlorine, and 166.2 mmol/L of phosphorus.

EXAMPLE 2

Neodymium chloride aqueous solution (15.0876 g) which is saturated at 20° C. was weighted out and added into a 150 ml reactor. Then 10 ml propanol was added into a round bottomed flask and mixed well. Subsequently, 19.6 ml (59.5 mmol) diisooctyl phosphite was measured out by a pipette and added into the above round bottomed flask. After mixed thoroughly, the mixed solution was in purple-red. The reactor was placed and heated to react in a 80° C. water bath for 2 h before vacuumed. Then propanol and water were removed, and the transparent purple-blue viscid reaction product was obtained. As the temperature of the water bath was adjusted to 50° C., 60 ml hexane was added and mixed in the round bottomed flask. The transparent purple-blue viscid reaction product dispersed into hexane gradually and formed a light purple-blue homogeneous phase hexane solution. All of the light purple-blue homogeneous phase hexane solution was transferred into a 100 ml volumetric flask and further diluted with hexane to reach the volumetric mark. After the constant volume was achieved, the hexane solution of the reaction product was sealed and stored in a long neck ampoule. Based on further analysis, it was found that the hexane solution of the reaction product contained 297.4 mmol/L of neodymium, 895.2 mmol/L of chlorine, and 588.9 mmol/L of phosphorus.

EXAMPLE 3

Ten milliliter of 1.0933M neodymium chloride aqueous solution was precisely measured out by a 10 ml pipette and added into a 250 ml-round bottomed flask, into which 150 ml methanol solution containing 32.8 mmol dimethyl phosphite was added and mixed well. The mixed solution was in purple-red. The round bottomed flask was placed and heated to react in a 70° C. water bath for 1.5 h before vacuumed. Then methanol and water were removed, and the transparent purple-blue viscid reaction product was obtained. As the reaction product was cooled down to room temperature, 150 ml tetrahydrofuran was added and mixed well in the round bottomed flask. The transparent purple-blue viscid reaction product dispersed into tetrahydrofuran gradually and formed a light purple-blue homogeneous phase tetrahydrofuran solution.

EXAMPLE 4-13

Same as Example 3, except for dialkyl phosphite and its usage amount, as well as the solvent to dissolve the reaction product, as shown in Table 1.

TABLE 1

| Example | dialkyl phosphite Name | Usage Amount (mmol) | Solvent | Color of the reaction product solution |
| --- | --- | --- | --- | --- |
| 4 | dimethyl phosphite | 5.5 | ethanol | transparent purple-red solution |
| 5 | diethyl phosphite | 656 | no | transparent purple-blue solution |
| 6 | dipropyl phosphite | 10.9 | ethanol | transparent purple-red solution |
| 7 | diisopropyl phosphite | 219 | no | transparent purple-blue solution |
| 8 | cycloethyl phosphite | 21.9 | ethanol | transparent purple-red solution |
| 9 | cyclopropyl phosphite | 32.8 | tetrahydrofuran | light purple-blue homogeneous phase solution |
| 10 | cyclobutyl phosphite | 65.6 | toluene | transparent purple-blue solution |
| 11 | cyclopentyl phosphite | 109 | no | transparent purple-blue solution |
| 12 | cycloisopentyl phosphite | 87.5 | xylene | transparent purple-blue solution |
| 13 | cyclohexyl phosphite | 43.7 | benzene | transparent purple-blue solution |

EXAMPLE 14-22

Same as Example 1, except for the usage amount of diisooctyl phosphite, the reaction temperature and the reaction period, as shown in Table 2.

TABLE 2

| Example | Usage amount of diisooctyl phosphite (mmol) | Reaction temperature (° C.) | Reaction period (min) | Color of the hexane solution of reaction product |
| --- | --- | --- | --- | --- |
| 14 | 10.9 | 100 | 10 | transparent purple-blue homogeneous phase solution |

TABLE 2-continued

| Example | Usage amount of diisooctyl phosphite (mmol) | Reaction temperature (° C.) | Reaction period (min) | Color of the hexane solution of reaction product |
|---|---|---|---|---|
| 15 | 21.9 | 60 | 30 | transparent purple-blue homogeneous phase solution |
| 16 | 32.8 | 70 | 20 | transparent purple-blue homogeneous phase solution |
| 17 | 43.7 | 30 | 480 | transparent purple-blue homogeneous phase solution |
| 18 | 65.6 | 40 | 240 | transparent purple-blue homogeneous phase solution |
| 19 | 87.5 | 80 | 60 | transparent purple-blue homogeneous phase solution |
| 20 | 109.3 | 10 | 360 | transparent purple-blue homogeneous phase solution |
| 21 | 32.8 | 20 | 720 | transparent purple-blue homogeneous phase solution |
| 22 | 43.7 | 100 | 5 | transparent purple-blue homogeneous phase solution |

EXAMPLE 23

Ten milliliter of 1.0933M neodymium chloride aqueous solution was precisely measured out by a 10 ml pipette and added into a 500 ml-round bottomed flask, into which 250 ml ethanol solution containing 32.8 mmol cyclodecyl phosphite was added and mixed well. The mixed solution was in purple-red. The round bottomed flask was placed and heated to react in a 120° C. oil bath. During the reaction, ethanol and water were removed, and then the transparent purple-blue viscid reaction product was obtained. As the temperature of the oil bath was adjusted to 40° C., 150 ml raffinate oil was added and mixed well in the round bottomed flask. The transparent purple-blue viscid reaction product dispersed into the raffinate oil gradually and formed a light purple-blue homogeneous phase raffinate oil solution. All of the light purple-blue homogeneous phase raffinate oil solution was transferred into a 200 ml volumetric flask and further diluted with raffinate oil to reach the volumetric mark. After the constant volume was achieved, the raffinate oil solution of the reaction product was sealed and stored in a long neck ampoule. Based on further analysis, it was found that the raffinate oil solution of the reaction product contained 53.8 mmol/L of neodymium, 159.3 mmol/L of chlorine, and 160.5 mmol/L of phosphorus.

EXAMPLE 24-38

Same as Example 23, except for the types of dialkyl phosphite, the reaction temperature and the aliphatic hydrocarbon solvent, as shown in Table 3.

TABLE 3

| Example | dialkyl phosphite formula | Reaction temperature (° C.) | Aliphatic hydrocarbon solvent | Color of the aliphatic hydrocarbon solution of reaction product |
|---|---|---|---|---|
| 24 | $H(O)P(OC_4H_9)_2$ | 105 | cyclohexane | transparent purple-blue homogeneous phase solution |
| 25 | $H(O)P(OC_5H_{11})_2$ | 105 | cyclohexane | transparent purple-blue homogeneous phase solution |
| 26 | $H(O)P(OC_6H_{13})_2$ | 110 | raffinate oil | transparent purple-blue homogeneous phase solution |
| 27 | $H(O)P(OC_7H_{15})_2$ | 105 | naphtha | transparent purple-blue homogeneous phase solution |
| 28 | $H(O)P(OC_8H_{17})_2$ | 120 | hexane | transparent purple-blue homogeneous phase solution |
| 29 | $H(O)P(OC_9H_{19})_2$ | 125 | nonane | transparent purple-blue homogeneous phase solution |
| 30 | $H(O)P(OC_{10}H_{21})_2$ | 130 | neopentane | transparent purple-blue homogeneous phase solution |

TABLE 3-continued

| Example | dialkyl phosphite formula | Reaction temperature (° C.) | Aliphatic hydrocarbon solvent | Color of the aliphatic hydrocarbon solution of reaction product |
|---|---|---|---|---|
| 31 | $H(O)P(OC_{12}H_{25})_2$ | 145 | hexane | transparent purple-blue homogeneous phase solution |
| 32 | $H(O)P(OC_{14}H_{29})_2$ | 150 | heptane | transparent purple-blue homogeneous phase solution |
| 33 | $H(O)P(OC_7H_{14}O)$ | 90 | cyclohexane | transparent purple-blue homogeneous phase solution |
| 34 | $H(O)P(OC_8H_{16}O)$ | 100 | cyclohexane | transparent purple-blue homogeneous phase solution |
| 35 | $H(O)P(OC_9H_{18}O)$ | 105 | naphtha | transparent purple-blue homogeneous phase solution |
| 36 | $H(O)P(OC_{10}H_{20}O)$ | 115 | octane | transparent purple-blue homogeneous phase solution |
| 37 | $H(O)P(OC_{11}H_{22}O)$ | 130 | raffinate oil | transparent purple-blue homogeneous phase solution |
| 38 | $H(O)P(OC_{12}H_{24}O)$ | 140 | neodecane | transparent purple-blue homogeneous phase solution |

EXAMPLE 39

Twenty milliliter of 0.5502M neodymium chloride aqueous solution was precisely measured out by a 20 ml pipette and added into a 500 ml-round bottomed flask, into which 50 ml ethanol was added and mixed well. Then 50 ml methanol solution containing 21.9 mmol cyclohexyl phosphite and 50 ml isopropanol solution containing 21.9 mmol diisooctyl phosphite were added and mixed well. The mixed solution was in purple-red. The round bottomed flask was placed and heated to react in a 90° C. water bath for 30 min. Then the mixed alcohol and water were removed, and the transparent purple-blue viscid reaction product was obtained. As the temperature of the water bath was adjusted to 50° C., 150 ml raffinate oil was added and mixed in the round bottomed flask. The transparent purple-blue viscid reaction product dispersed into raffinate oil gradually and formed a light purple-blue homogeneous phase raffinate oil solution. All of the light purple-blue homogeneous phase raffinate oil solution was transferred into a 200 ml volumetric flask and further diluted with raffinate oil to reach the volumetric mark. After the constant volume was achieved, the raffinate oil solution of the reaction product was sealed and stored in a long neck ampoule. Based on further analysis, it was found that the raffinate oil solution of the reaction product contained 54.1 mmol/L of neodymium, 161.8 mmol/L of chlorine, and 214.6 mmol/L of phosphorus.

EXAMPLE 40

Ten milliliter of 2.2045M neodymium chloride aqueous solution was precisely measured out by a 10 ml pipette and added into a 250 ml-round bottomed flask, into which 30 ml ethanol was added and mixed well. Then 18.2 ml diisooctyl phosphite was added and mixed well. The mixed solution was in purple-red. The round bottomed flask was placed and heated to react in a 80° C. water bath for 20 min. Then ethanol and water were removed, and the transparent purple-blue viscid reaction product was obtained. As the temperature of the water bath was adjusted to 50° C., 150 ml hexane was added and mixed well in the round bottomed flask. The transparent purple-blue viscid reaction product dispersed into raffinate oil gradually and formed a light purple-blue homogeneous phase raffinate oil solution.

The invention claimed is:

1. A method for producing soluble neodymium chloride complex, comprising:

mixing neodymium chloride aqueous solution, alcohol and dialkyl phosphite in a reactor to form a homogeneous phase system;

letting the system to react at a temperature of 10-150° C. for 5 minutes to 12 hours, wherein a molar ratio of dialkyl phosphite to neodymium chloride is in a range of 0.5-60, and a ratio of the alcohol to the neodymium chloride aqueous solution is in a range of 3.0-30 by volume; and removing water and alcohol out of the system to obtain a neodymium chloride-dialkyl phosphite complex;

wherein said neodymium chloride aqueous solution is saturated or nonsaturated neodymium chloride aqueous solution;

said alcohol is selected from the group consisting of methanol, ethanol, propanol, and any mixtures thereof;

said dialkyl phosphite has a structure shown by the following formula:

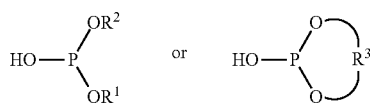

$R^1$ and $R^2$ each independently represents alkyl group with 1 or more carbon atoms, $R^3$ is an alkylidene group with 2 or more carbon atoms.

2. The method for producing soluble neodymium chloride complex according to claim 1, wherein said reaction temperature is 20-100° C.

3. The method for producing soluble neodymium chloride complex according to claim 1, wherein said molar ratio of the dialkyl phosphite to neodymium chloride is in a range of 1.0-10.

4. The method for producing soluble neodymium chloride complex according to claim 1, wherein said alcohol is ethanol.

5. The method for producing soluble neodymium chloride complex according to claim 1, wherein in the formula of said dialkyl phosphite, $R^1$ and $R^2$ each independently has 4 or more carbon atoms, $R^3$ has 7 or more carbon atoms.

* * * * *